United States Patent
Sievert et al.

(10) Patent No.: US 8,232,435 B2
(45) Date of Patent: *Jul. 31, 2012

(54) 1,2,3,3,3-PENTAFLUOROPROPENE PRODUCTION PROCESSES

(75) Inventors: Allen Capron Sievert, Elkton, MD (US); Mario Joseph Nappa, Newark, DE (US); Barry Asher Mahler, Glen Mills, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 371 days.

This patent is subject to a terminal disclaimer.

(21) Appl. No.: 12/440,046

(22) PCT Filed: Sep. 5, 2007

(86) PCT No.: PCT/US2007/019316
§ 371 (c)(1),
(2), (4) Date: Mar. 25, 2009

(87) PCT Pub. No.: WO2008/030441
PCT Pub. Date: Mar. 13, 2008

(65) Prior Publication Data
US 2009/0306438 A1 Dec. 10, 2009

Related U.S. Application Data

(60) Provisional application No. 60/842,446, filed on Sep. 5, 2006.

(51) Int. Cl.
C07C 17/00 (2006.01)
(52) U.S. Cl. ........................................ 570/156
(58) Field of Classification Search ................ 570/156
See application file for complete search history.

(56) References Cited

U.S. PATENT DOCUMENTS

| | | |
|---|---|---|
| 3,258,500 A | 6/1966 | Swamer, et al. |
| 4,766,260 A | 8/1988 | Manzer et al. |
| 4,828,818 A | 5/1989 | Carlson et al. |
| 4,902,838 A | 2/1990 | Manzer et al. |
| 4,978,649 A | 12/1990 | Surovikin et al. |
| 5,036,036 A | 7/1991 | Lerou |
| 5,136,113 A | 8/1992 | Rao et al. |
| 5,268,122 A | 12/1993 | Rao et al. |
| 5,396,000 A | 3/1995 | Nappa et al. |
| 5,532,418 A | 7/1996 | Nakada et al. |
| 6,031,141 A | 2/2000 | Mallikarjuna et al. |
| 6,369,284 B1 | 4/2002 | Nappa et al. |
| 7,217,678 B2 | 5/2007 | Rao et al. |
| 2005/0228202 A1 | 10/2005 | Nappa et al. |
| 2006/0106263 A1 | 5/2006 | Miller et al. |
| 2006/0110618 A1 | 5/2006 | Manivannan et al. |
| 2007/0100174 A1 | 5/2007 | Miller et al. |
| 2010/0004492 A1* | 1/2010 | Nappa et al. ............... 570/136 |

FOREIGN PATENT DOCUMENTS

| | | |
|---|---|---|
| EP | 0644173 A1 | 3/1995 |
| WO | 9427940 A1 | 12/1994 |
| WO | 2007053688 A2 | 5/2007 |
| WO | 2007117391 A1 | 10/2007 |
| WO | 2008008350 A2 | 1/2008 |
| WO | WO 2008/008350 A2 * | 1/2008 |
| WO | 9605157 A1 | 2/2009 |

OTHER PUBLICATIONS

U.S. Appl. No. 60/819,150, filed Jul. 7, 2006, Applicant: Xuehui Sun et al.
U.S. Appl. No. 60/732,041, filed Nov. 1, 2005, Applicant: Ralph Newton Miller et al.
U.S. Appl. No. 60/839,737, filed Aug. 24, 2006, Applicant: Jeffrey P. Knapp et al.
Knunyants et al., Reactions PF Fluoro Olefins Communication 13. Catalytic Hydrogenation of Perfluoro Olefins, Bulletin of the Academy of Sciences of the USSR, Division of Chemical Sciences, 1960, pp. 1312-1317.

* cited by examiner

Primary Examiner — Jafar Parsa

(57) ABSTRACT

The present disclosure relates to a new and efficient manufacturing process for the production of HFC-1225ye. The process involves contacting at least one hexafluoropropane selected from the group consisting of 1,1,1,2,2,3-hexafluoropropane and 1,1,1,2,3,3-hexafluoropropane with a suitable catalyst in a reactor to obtain a product mixture containing HFC-1225ye (1,2,3,3,3-pentafluoropropene) where the pressure in the reactor ranges from about 0.5 psig to about 100 psig.

13 Claims, No Drawings

1,2,3,3,3-PENTAFLUOROPROPENE PRODUCTION PROCESSES

This application represents a national filing under 35 U.S.C. 371 of International Application No. PCT/US2007/19316 filed Sep. 5, 2007, and claims priority of U.S. Provisional Application No. 60/842,446 filed Sep. 5, 2006.

BACKGROUND OF THE INVENTION

1. Field of the Disclosure

The disclosure herein relates in general to processes for the catalytic dehydrofluorination of 1,1,1,2,3,3-hexafluoropropane (HFC-236ea) or 1,1,1,2,2,3-hexafluoropropane (HFC-236cb) to make 1,2,3,3,3-pentafluoropropene (HFC-1225ye).

2. Description of Related Art

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFC-1225ye, having zero ozone depletion and a low global warming potential, has been identified as a potential refrigerant. U.S. Pat. No. 5,396,000 discloses a process for producing HFC-1225ye by the dehydrofluorination of HFC-236ea. Thus, there is a need for new manufacturing processes for the production of HFC-1225ye.

SUMMARY OF THE INVENTION

The present disclosure relates to a new and efficient manufacturing process for the production of HFC-1225ye. The process comprises contacting at least one hexafluoropropane selected from the group consisting of 1,1,1,2,2,3-hexafluoropropane and 1,1,1,2,3,3-hexafluoropropane with a suitable catalyst in a reactor to obtain a product mixture containing HFC-1225ye (1,2,3,3,3-pentafluoropropene) where the pressure in the reactor ranges from about 0.5 psig to about 100 psig. The foregoing general description and the following detailed description are exemplary and explanatory only and are not restrictive of the invention, as defined in the appended claims.

DETAILED DESCRIPTION OF THE INVENTION

Before addressing details of embodiments described below, some terms are defined or clarified.

HFC-1225ye may exist as one of two configurational isomers, E or Z. HFC-1225ye as used herein refers to the isomers, E-HFC-1225ye (CAS reg no. 5595-10-8) or Z-HFC-1225ye (CAS reg. no. 552843-8), as well as any combinations or mixtures of such isomers.

The term "amorphous" is intended to mean that there is no substantial peak in a X-ray diffraction pattern of the subject solid.

The term "hexafluoropropane" is intended to mean a partially fluorinated propane represented by the formula $C_3H_2F_6$. In one embodiment of this invention, a hexafluoropropane is selected from the group consisting of HFC-236cb and HFC-236ea.

The term "a suitable catalyst" is intended to mean a dehydrofluorination catalyst which can be used to convert HFC-236cb or HFC-236ea to HFC-1225ye.

The term "ppm" is intended to mean parts per million. The term "ppm-w" is intended to mean part per million by weight. The term "ppm-m" is intended to mean parts per million on a molar basis.

Generally, the dehydrofluorination reactions in the embodiments of this invention may be carried out using any dehydrofluorination catalyst known in the art. These catalysts include, but are not limited to, aluminum fluoride; fluorided alumina; metals on aluminum fluoride; metals on fluorided alumina; oxides, fluorides, and oxyfluorides of magnesium; oxides, fluorides, and oxyfluorides of zinc; oxides, fluorides, and oxyfluorides of the mixtures of magnesium and zinc and/or aluminum; lanthanum oxide and fluorided lanthanum oxide; chromium oxides, fluorided chromium oxides, and cubic chromium trifluoride; crystalline cobalt-substituted alpha-chromium oxides where from about 0.05 atom % to about 6 atom % of the chromium atoms in the alpha-chromium oxide lattice are replaced by trivalent cobalt atoms; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

Dehydrofluorination catalysts include aluminum fluoride, fluorided alumina, metals on aluminum fluoride, and metals on fluorided alumina, as disclosed in U.S. Pat. No. 5,396,000, incorporated herein by reference. Fluorided alumina and aluminum fluoride can be prepared as described in U.S. Pat. No. 4,902,838, incorporated herein by reference. Suitable metals include chromium, magnesium (e.g., magnesium fluoride), Group VIIB metals (e.g., manganese), Group IIIB metals (e.g., lanthanum), and zinc. In use, such metals are normally present as halides (e.g., fluorides), as oxides and/or as oxyhalides. Metals on aluminum fluoride and metals on fluorided alumina can be prepared by procedures as described in U.S. Pat. No. 4,766,260, incorporated herein by reference. In one embodiment, when supported metals are used, the total metal content of the catalyst is from about 0.1 to 20 percent by weight, typically from about 0.1 to 10 percent by weight. Preferred catalysts include catalysts consisting essentially of aluminum fluoride and/or fluorided alumina.

Additionally, dehydrofluorination catalysts include oxides, fluorides, and oxyfluorides of magnesium; oxides, fluorides, and oxyfluorides of zinc; oxides, fluorides, and oxyfluorides of the mixtures of magnesium and zinc and/or aluminum. Such suitable catalysts may be prepared, for example by drying magnesium oxide until essentially all water is removed, e.g., for about 18 hours at about 100° C. The dried material is then transferred to the reactor to be used. The temperature is then gradually increased to about 400° C. while maintaining a flow of nitrogen through the reactor to remove any remaining traces of moisture from the magnesium oxide and the reactor. The temperature is then lowered to about 200° C. and a fluoriding agent, such as HF, or other vaporizable fluorine containing compounds such as HF, $SF_4$, $CCl_3F$, $CCl_2F_3$, $CHF_3$, $CHClF_2$ or $CCl_2FCClF_2$, optionally diluted with an inert gas such as nitrogen, is passed through the reactor. The inert gas or nitrogen can be gradually reduced until only HF or other vaporizable fluorine containing compounds is being passed through the reactor. At this point, the temperature can be increased to about 450° C. and held at that temperature to convert the magnesium oxide to a fluoride content corresponding to at least 40 percent by weight, e.g., for 15 to 300 minutes, depending on the fluoriding agent flowrate and the catalyst volume. The fluorides are in the form of magnesium fluoride or magnesium oxyfluoride; the remainder of the catalyst is magnesium oxide. It is understood in the art that fluoriding conditions such as time and temperature can be adjusted to provide higher than 40 percent by weight fluoride-containing material.

Another suitable procedure for the catalyst preparation is to add ammonium hydroxide to a solution of magnesium nitrate and, if present, zinc nitrate and/or aluminum nitrate. The ammonium hydroxide is added to the nitrate solution to a pH of about 9.0 to 9.5. At the end of the addition, the solution is filtered, the solid obtained is washed with water, dried and slowly heated to 500° C., where it is calcined. The calcined product is then treated with a suitable fluorine-containing compound as described above.

Yet another procedure for the preparation of metal (i.e., magnesium, optionally containing also zinc and/or aluminum) fluoride catalysts containing one or more metal fluorides is to treat an aqueous solution of the metal(s) halide(s) or nitrate(s) in deionized water with 48 percent aqueous HF with stirring. Stirring is continued overnight and the slurry evaporated to dryness on a steam bath. The dried solid is then calcined in air at 400° C. for about four hours, cooled to room temperature, crushed and sieved to provide material for use in catalyst evaluations.

Additionally, dehydrofluorination catalysts include lanthanum oxide and fluorided lanthanum oxide.

Suitable fluorided lanthanum oxide compositions may be prepared in any manner analogous to those known to the art for the preparation of fluorided alumina. For example, the catalyst composition can be prepared by fluorination of lanthanum oxide.

Suitable catalyst compositions may also be prepared by precipitation of lanthanum as the hydroxide, which is thereafter dried and calcined to form an oxide, a technique well known to the art. The resulting oxide can then be pretreated as described herein.

The catalyst composition can be fluorinated to the desired fluorine content by pretreatment with a fluorine-containing compound at elevated temperatures, e.g., at about 200° C. to about 450° C. The pretreatment with a vaporizable fluorine-containing compound such as HF, $SF_4$, $CCl_3F$, $CCl_2F_3$, $CHF_3$, $CHClF_2$ or $CCl_2FCClF_2$ can be done in any convenient manner including in the reactor which is to be used for carrying out the dehydrofluorination reaction. By vaporizable fluorine-containing compound is meant a fluorine containing compound which, when passed over the catalyst at the indicated conditions, will fluorinate the catalyst to the desired degree.

A suitable catalyst may be prepared, for example, by drying $La_2O_3$ until essentially all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and the vaporizable fluorine-containing compound is passed through the reactor. If necessary, nitrogen or other inert gases can be used as diluents. The $N_2$ or other inert diluents can be gradually reduced until only the vaporizable fluorine-containing compound is being passed through the reactor. At this point the temperature can be increased to about 450° C. and held at that temperature to convert the $La_2O_3$ to a fluorine content corresponding to at least 80 percent $LaF_3$ by weight, e.g., for 15 to 300 minutes, depending on the flow of the fluorine containing compound and the catalyst volume.

Another suitable procedure for the catalyst preparation is to add ammonium hydroxide to a solution of $La(NO_3)_3 6H_2O$. The ammonium hydroxide is added to the nitrate solution to a pH of about 9.0 to 9.5. At the end of the addition, the solution is filtered, the solid obtained is washed with water, and slowly heated to about 400° C., where it is calcined. The calcined product is then treated with a suitable vaporizable fluorine-containing compound as described above.

Additionally, dehydrofluorination catalysts include chromium oxide ($Cr_2O_3$), fluorided chromium oxide, and cubic chromium trifluoride. Cubic chromium trifluoride may be prepared from $CrF_3 XH_2O$, where X is 3 to 9, preferably 4, by heating in air or an inert atmosphere (e.g., nitrogen or argon) at a temperature of about 350° C. to about 400° C. for 3 to 12 hours, preferably 3 to 6 hours.

$Cr_2O_3$ is commercially available from Engelhard Corporation (101 Wood Avenue, P.O. Box 770, Iselin, N.J. 08830-0770).

$Cr_2O_3$ can also be prepared by pyrolysis of ammonium dichromate as disclosed in U.S. Pat. No. 5,036,036, which is incorporated herein by reference.

$Cr_2O_3$ can also be prepared by the reaction of chromium (VI) oxide with a reducing solvent, such as methanol, as disclosed in U.S. Pat. No. 4,828,818, which is incorporated herein by reference.

$Cr_2O_3$ can also be prepared by reducing chromium (VI) oxide in water with a suitable reducing agent, such as ethanol, as disclosed in U.S. Pat. No. 3,258,500, which is incorporated herein by reference.

The amount of potassium and other alkali metals in $Cr_2O_3$ can be reduced by a water washing step as disclosed in U.S. Pat. No. 5,036,036.

In one embodiment of this invention, the $Cr_2O_3$ catalyst has surface areas of about 20 $m^2/g$ to about 500 $m^2/g$.

In another embodiment of this invention, the $Cr_2O_3$ catalyst has surface areas of about 40 $m^2/g$ to about 350 $m^2/g$.

In another embodiment of this invention, the $Cr_2O_3$ catalyst has surface areas of about 60 $m^2/g$ to about 300 $m^2/g$.

In another embodiment of this invention, the $Cr_2O_3$ catalyst has surface areas of about 100 $m^2/g$ to about 300 $m^2/g$.

In one embodiment of this invention, the $Cr_2O_3$ catalyst contains an alkali metal content of about 2000 ppm-w or less.

In another embodiment of this invention, the $Cr_2O_3$ catalyst contains an alkali metal content of about 300 ppm-w or less.

In another embodiment of this invention, the $Cr_2O_3$ catalyst contains an alkali metal content of about 100 ppm-w or less.

In one embodiment of this invention, the $Cr_2O_3$ catalyst is amorphous.

In another embodiment of this invention, the $Cr_2O_3$ catalyst is crystalline $\alpha$-$Cr_2O_3$.

The fluorided chromium oxide catalysts can be made by treating $Cr_2O_3$ with HF, $CCl_3F$ or hydrofluorocarbons. In one embodiment of this invention, a fluorided chromium oxide catalyst is made by treating dry $Cr_2O_3$ with a fluorination agent such as $CCl_3F$ or HF. This treatment can be accomplished by placing the $Cr_2O_3$ in a suitable container (which can be the reactor to be used to perform the dehydrofluorination reaction) and thereafter passing HF over the dry $Cr_2O_3$ for a suitable period of time (e.g., about 15 to 300 minutes) at a suitable temperature (e.g., about 200° C. to 450° C.).

In another embodiment of this invention, a fluorided chromium oxide catalyst is made by treating $Cr_2O_3$ with a hydrofluorocarbon at an elevated temperature.

In another embodiment of this invention, a fluorided chromium oxide catalyst is made in situ. For example, the reactant HFC-236cb, HFC-236ea can be employed in the formation of a fluorided chromium oxide catalyst by heating together with $Cr_2O_3$ in the reactor.

Cubic chromium trifluoride is useful by itself, or together with other chromium compounds, as a dehydrofluorination catalyst. Preparation of cubic chromium trifluoride is described in U.S. Pat. No. 6,031,141, incorporated herein by reference. Of note are catalyst compositions comprising chromium wherein at least 10 weight percent of the chromium is in the form of cubic chromium trifluoride, particularly catalyst compositions wherein at least 25 percent of the chromium is in the form of cubic chromium trifluoride, and especially catalyst compositions wherein at least 60 percent of the chromium is in the form of cubic chromium trifluoride. The chromium, including the cubic chromium trifluoride can be supported on and/or physically mixed with materials such as carbon, aluminum fluoride, fluorided alumina, lanthanum fluoride, magnesium fluoride, calcium fluoride, zinc fluoride and the like. Preferred are combinations including cubic chromium trifluoride in combination with magnesium fluoride and/or zinc fluoride.

Additionally, dehydrofluorination catalysts include crystalline cobalt-substituted alpha-chromium oxides where from about 0.05 atom % to about 6 atom % of the chromium atoms in the alpha-chromium oxide lattice are replaced by trivalent cobalt atoms. Such catalysts are disclosed in U.S. Pat. No. 7,217,678, incorporated herein by reference.

Additionally, dehydrofluorination catalysts include activated carbon, or three dimensional matrix carbonaceous materials as disclosed in U.S. Pat. No. 6,369,284, incorporated herein by reference; or carbon or metals such as sodium, potassium, rubidium, cesium, yttrium, lanthanum, cerium, praseodymium, neodymium, samarium, chromium, iron, cobalt, rhodium, nickel, copper, zinc, and mixtures thereof, supported on carbon as disclosed in U.S. Pat. No. 5,268,122, incorporated herein by reference. Carbon from any of the following sources are useful for the process of this invention; wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™, Columbia LCK™, Calgon PCB, Calgon BPL™, Westvaco™, Norit™, and Barnaby Cheny NB™.

Carbon includes acid-washed carbon (e.g., carbon which has been treated with hydrochloric acid or hydrochloric acid followed by hydrofluoric acid). Acid treatment is typically sufficient to provide carbon that contains less than 1000 ppm-w of ash. Suitable acid treatment of carbon is described in U.S. Pat. No. 5,136,113, incorporated herein by reference. The carbon also includes three dimensional matrix porous carbonaceous materials. Examples are those described in U.S. Pat. No. 4,978,649, incorporated herein by reference. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

The physical shape of the catalyst is not critical and may, for example, include pellets, powders or granules. Additionally, for catalysts supported on carbon, the carbon may be in the form of powder, granules, or pellets, or the like. Although not essential, catalysts that have not been fluorided may be treated with HF before use. It is thought that this converts some of the surface oxides to oxyfluorides. This pretreatment can be accomplished by placing the catalyst in a suitable container (which can be the reactor to be used to perform the reaction of the instant invention) and thereafter, passing HF over the dried catalyst so as to partially saturate the catalyst with HF. This is conveniently carried out by passing HF over the catalyst for a period of time (e.g., about 15 to 300 minutes) at a temperature of, for example, about 200° C. to about 450° C.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

A process has been provided to produce HFC-1225ye. The process comprises contacting at least one hexafluoropropane selected from the group consisting of HFC-236cb and HFC-236ea with a suitable catalyst in a reactor to obtain a product mixture comprising HFC-1225ye, wherein the pressure in the reactor ranges from about 0.5 psig to about 100 psig. In another embodiment of this invention, the pressure in the reactor ranges from about 15 psig to about 60 psig. In another embodiment of this invention, the pressure in the reactor ranges from about 15 psig to about 45 psig.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The reactors used in the processes of embodiments of this invention may be a single packed bed or a shell-in-tube design. The preferred design is a shell-in-tube reactor with catalyst packed inside the tubes, and a heat carrier fluid circulating shell side to help maintain the reaction zone at the desired temperature. Any heat carrier fluid suitable for providing reactor operation at temperatures of 200° C. to 400° C. is acceptable. Acceptable heat carrier fluids include Air, Nitrogen, Therminol (sold by Solutia) and molten salts (such as Hytec Salts).

HFC-236ea can be synthesized by a variety of methods. For example, HFC-236ea may be obtained by reacting tetrafluorochloropropene with HF as described by Nakada et al. in U.S. Pat. No. 5,532,418.

HFC-236cb can be synthesized by a variety of methods. For example, HFC-236cb may be obtained by reacting tetrafluoroethylene (TFE) with difluoromethane (HFC-32) as described in U.S. Application No. 60/819,150, filed on Jul. 7, 2006.

In one embodiment of the invention, the reaction temperature is from about 200° C. to about 400° C.

In another embodiment of the invention, the contact time is from about 1 second to about 300 seconds.

In another embodiment of the invention, the contact time is from about 30 second to about 100 seconds.

In another embodiment of the invention, HFC-236ea alone is used as the starting material, and the reaction temperature is from about 200° C. to about 350° C.

In another embodiment of the invention, HFC-236cb alone is used as the starting material, and the reaction temperature is from about 250° C. to about 400° C.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Optionally, the catalytic dehydrofluorination reactions in the embodiments of this invention can be carried out in the presence of an inert gas such as nitrogen, helium, or argon. The addition of an inert gas can be used to increase the extent of dehydrofluorination. Of note are processes where the mole ratio of inert gas to hexafluoropropane undergoing dehydrofluorination is from about 5:1 to about 1:1. In one embodiment of this invention, the reaction is carried out in the presence of nitrogen.

Generally, the product mixture may contain HF, HFC-1225ye, unreacted HFC-236cb and unreacted HFC-236ea.

In one embodiment of this invention, HFC-1225ye present in the product mixture may be separated from the other components of the product mixture and unreacted starting materials by fractional distillation. When HF is also present in the product mixture, this separation can also include isolation of an azeotrope or near azeotrope of HFC-1225ye and HF and further processing to produce HF-free HFC-1225ye by using procedures similar to that disclosed in US Patent Publication US 2006/0106263 A1, which is incorporated herein by reference.

U.S. Application No. 60/732,041, filed on Nov. 1, 2005 and incorporated herein by reference, discloses an azeotrope or near-azeotrope composition of Z-HFC-1225ye and HF.

Unreacted starting material can be recycled to the reactor for the production of additional HFC-1225ye. In one embodiment of this invention, HFC-236cb and/or HFC-236ea is recovered from the product mixture by fractional distillation and recycled to the reactor.

In one embodiment of this invention, HFC-236cb is fed to one reactor for the production of HFC-1225ye (hereafter referred to as the HFC-236cb reactor), and HFC-236ea is fed to another reactor for the production of HFC-1225ye (hereafter referred to as the HFC-236ea reactor). The product mixtures from both reactors may be combined or processed separately. HFC-236cb recovered from the product mixtures will be recycled to the HFC-236cb reactor. HFC-236ea recovered from the product mixtures will be recycled to the HFC-236ea reactor. The HFC-236ea and the HFC-236cb reactors can be operated under different conditions. For example, the HFC-236ea reactor can operate at 200-350 deg C., while the HFC-236cb reactor can operate at 250400 deg C. For example, the HFC-236ea reactor can operate using a catalyst comprising alumina, while the HFC-236cb reactor can operate using a catalyst comprising chrome.

In one embodiment of this invention, HF present in the product mixture may be separated from the other components of the product mixture and unreacted starting materials by an azeotropic distillation process with an entrainer similar to that disclosed in U.S. Application No. 60/839,737, filed on Aug. 24, 2006 and incorporated herein by reference.

In one embodiment of this invention, HFC-1225ye is recovered as a product containing no more than 100 ppm-m HF.

In another embodiment of this invention, HFC-1225ye is recovered as a product containing no more than 10 ppm-m HF.

In another embodiment of this invention, HFC-1225ye is recovered as a product containing no more than 1 ppm-m HF.

In one embodiment of this invention, HF is removed from at least one of the feed stream or recycle stream such that a feed stream or recycle stream containing no more than 100 ppm-m HF is fed to the reactor.

In another embodiment of this invention, HF is removed from at least one of the feed stream or recycle stream such that a feed stream or recycle stream containing no more than 10 ppm-m HF is fed to the reactor.

In another embodiment of this invention, HF is removed from the feed stream or recycle stream such that a feed steam or recycle stream containing no more than 1 ppm-m HF is fed to the reactor.

Optionally, entraining agents, such as ethane and propane, may be co-fed to the reactor. In one embodiment of this invention, the product mixture containing entraining agents can be sent to the distillation column wherein HF can be separated from HFC-1225ye. Said entraining agents facilitate the separation of the HF from the HFC-1225ye. Said entraining agents are described in U.S. Application No. 60/839,737, filed on Aug. 24, 2006 and incorporated herein by reference In one embodiment of this invention, difluoromethane (HFC-32) can be co-fed to the reactor.

As described in U.S. Application No. 60/819,150, filed on Jul. 7, 2006, HFC-236cb can be produced by reaction of TFE and HFC-32, where the HFC-236cb product mixture contains HFC-236cb and HFC-32. Such HFC-236cb product mixture can be fed to the reactor used in the embodiments of this invention to make HFC-1225ye. HFC-32 present in the HFC-1225ye product mixture may optionally be recovered and recycled back for the production of HFC-236cb. Optionally, HFC-32 may be left in the HFC-1225ye product mixture.

Optionally, the dehydrofluorination reactions in the processes applied in the embodiments of this invention can be done in the presence of oxygen or air. In another embodiment of the invention, air or oxygen is co-fed with the reactant into the reactor.

Optionally, a scavenger is added to the reactor to remove HF from the product mixture.

The term "a scavenger" is intended to mean a chemical compound or a mixture of chemical compounds which can react with HF in the reactor under the conditions applied in the embodiments of this invention.

Examples of scavengers include hexafluoropropylene ($CF_3CF=CF_2$ or HFP), tetrafluoroethylene ($CF_2=CF_2$ or TFE), methylene chloride ($CH_2Cl_2$ of HCC-30) and methyl chloroform ($CH_3CCl_3$ or HCC-140).

At least one of the reactor feed stream, product mixture, or recycle stream of the embodiments of this invention may also contain 1,1,3,3,3-pentafluoropropene (HFC-1225zc). Optionally, HFC-1225zc can be removed from the feed stream, product mixture or recycle stream as described in FL1186, filed in Russia on Apr. 3, 2006 with a file number 2006110618.

At least one of the feed stream, product mixture, or recycle stream of the embodiments of this invention may also contain 1,1,1,3,3,3-Hexafluoropropane ($CF_3CH_2CF_3$ or 236fa). Optionally, HFC-236fa can be removed from the feed stream, product mixture, or recycle stream by distillation.

The term "deactivation" is intended to mean that the one-pass conversion of the HFC-236ea or HFC-236cb starting materials to the HFC-1225ye product at a given set of conditions (temperature, pressure, and feed material feed rates) is decreasing over time or has decreased compared to the initial performance of the reaction system.

Deactivated catalyst can be regenerated by exposing the catalysts to a variety of regenerating agents at elevated temperatures. Examples of regenerating agents include: Chlorine/HCl mixtures, Chlorine, Fluorine, oxygen and air. In one embodiment of this invention, the deactivated catalyst is exposed to the regenerating agent at or above 200° C. In another embodiment of this invention, the deactivated catalyst is exposed to the regenerating agent at or above 300° C. In another embodiment of this invention, the deactivated catalyst is exposed to the regenerating agent at or above 400° C.

What is claimed is:

1. A process, comprising: contacting 1,1,1,2,2,3-hexafluoropropane with a suitable catalyst in a reactor to obtain a product mixture comprising 1,2,3,3,3-pentafluoropropene, wherein the pressure in said reactor ranges from about 0.5 psig to about 100 psig.

2. The process of claim 1 wherein said pressure ranges from about 15 psig to about 60 psig.

3. The process of claim 1 wherein said pressure ranges from about 15 psig to about 45 psig.

4. The process of claim 1 further comprising: recovering 1,2,3,3,3-pentafluoropropene containing no more than 100 ppm-m HF from said product mixture.

5. The process of claim 1 further comprising: recovering 1,2,3,3,3-pentafluoropropene containing no more than 10 ppm-m HF from said product mixture.

6. The process of claim 1 further comprising: recovering 1,2,3,3,3-pentafluoropropene containing no more than 1 ppm-m HF from said product mixture.

7. The process of claim 1 wherein said suitable catalyst is selected from the group consisting of aluminum fluoride, fluorided alumina, metals on aluminum fluoride, and metals on fluorided alumina.

8. The process of claim 1 wherein said suitable catalyst is selected from the group consisting of magnesium oxides, magnesium fluorides, magnesium oxyfluorides, calcium oxides, calcium fluorides, calcium oxyfluorides, zinc oxides, zinc fluorides, zinc oxyfluorides, and mixtures thereof.

9. The process of claim 1 wherein said suitable catalyst is selected from the group consisting of lanthanum oxides and fluorided lanthanum oxides.

10. The process of claim 1 wherein said suitable catalyst is selected from the group consisting of chromium oxides, fluorided chromium oxides, and cubic chromium trifluoride.

11. The process of claim 1 wherein said suitable catalyst is a crystalline cobalt-substituted alpha-chromium oxide where from about 0.05 atom % to about 6 atom % of the chromium atoms in the alpha-chromium oxide lattice are replaced by trivalent cobalt atoms.

12. The process of claim 1 wherein said suitable catalyst is selected from the group consisting of carbon, acid-washed carbon, activated carbon, and three dimensional matrix carbonaceous materials.

13. The process of claim 1 wherein said suitable catalyst comprises a metal compound supported on carbon wherein said metal compound is an oxide, a fluoride, or an oxyfluoride of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

* * * * *